(12) United States Patent
Jones et al.

(10) Patent No.: US 7,335,287 B2
(45) Date of Patent: Feb. 26, 2008

(54) SOLID ELECTROLYTE SENSOR FOR MONITORING THE CONCENTRATION OF AN ELEMENT IN A FLUID PARTICULARLY MOLTEN METAL

(75) Inventors: Ivor W Jones, Chester (GB); Glyn Atherton, Cheshire (GB); Francis M Stackpool, Cheshire (GB)

(73) Assignees: Foseco International Limited, Staffordshire (GB); Ionotec Limited, Cheshire (GB)

( * ) Notice: Subject to any disclaimer, the term of this patent is extended or adjusted under 35 U.S.C. 154(b) by 865 days.

(21) Appl. No.: 10/472,935

(22) PCT Filed: Mar. 25, 2002

(86) PCT No.: PCT/GB02/01448

§ 371 (c)(1),
(2), (4) Date: Dec. 4, 2003

(87) PCT Pub. No.: WO02/079772

PCT Pub. Date: Oct. 10, 2002

(65) Prior Publication Data

US 2004/0084328 A1    May 6, 2004

(30) Foreign Application Priority Data

Mar. 28, 2001  (GB) ................................ 0107724.7

(51) Int. Cl.
*G01N 27/406* (2006.01)
(52) U.S. Cl. .................. 204/422; 204/421; 205/781.5; 205/783.5
(58) Field of Classification Search ............... 204/424, 204/427, 421, 422, 423; 205/781.5, 783.5
See application file for complete search history.

(56) References Cited

U.S. PATENT DOCUMENTS

| 3,657,094 A | 4/1972 | Hans et al. |
| 3,882,012 A * | 5/1975 | Dickinson et al. .......... 204/412 |
| 4,218,297 A * | 8/1980 | Henault et al. ............. 204/426 |

(Continued)

FOREIGN PATENT DOCUMENTS

| EP | 0 468 500 | 1/1992 |
| GB | 1 522 252 | 8/1978 |

OTHER PUBLICATIONS

Joglekar et al, Canadian Metallurgical Quarterly, 12(2), 1973, pp. 155-158.*

(Continued)

*Primary Examiner*—Kaj K. Olsen
(74) *Attorney, Agent, or Firm*—Nixon & Vanderhye P.C.

(57) ABSTRACT

The present invention relates to an electrochemical sensor for determining the concentration of a group IA metal in a fluid such as molten metal. The sensor comprises a substantially pure quantity of the group 1A metal as a reference electrode (13) contained in a sensor housing (3), and a solid electrolyte constituting at least part of the sensor housing (3). The electrolyte is in electrical contact with the reference electrode (13) and the sensor is capable of operating at temperatures in excess of 973K. In a preferred arrangement, the sensor comprises a two part elongate conductor (15), a first part (17) of which extends from the reference electrode (13) into a refractory seal (11*a*), and a second part (19) of which extends from within the refractory seal (11*a*) externally of the sensor, the two parts (17, 19) being welded together.

8 Claims, 9 Drawing Sheets

U.S. PATENT DOCUMENTS

Figure 1:
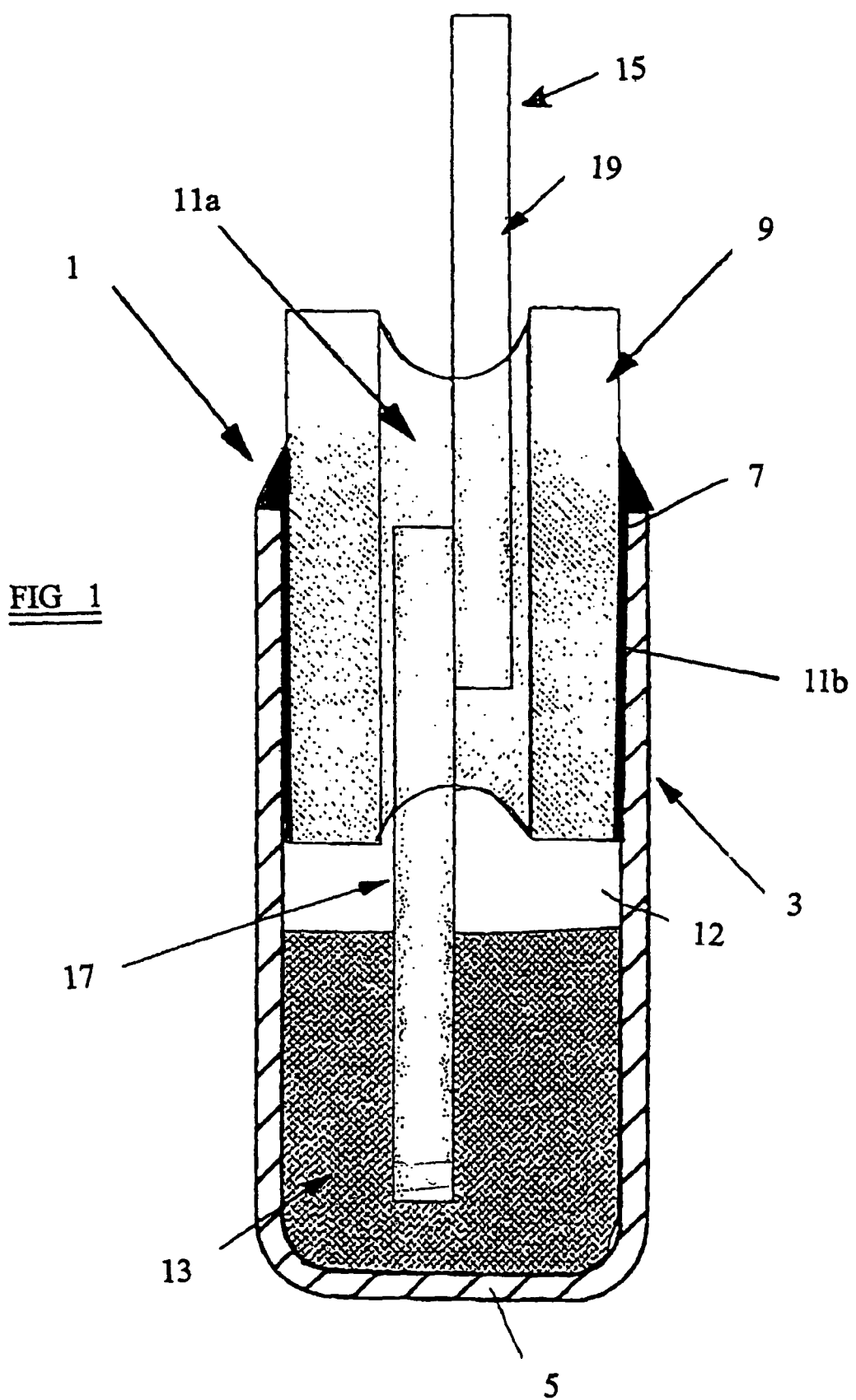

| | | |
|---|---|---|
| 4,645,571 A | 2/1987 | Dubreuil et al. |
| 4,906,349 A * | 3/1990 | Beatrice et al. ............. 204/422 |
| 5,336,389 A | 8/1994 | Dubreil |
| 5,656,143 A | 8/1997 | Swetmam et al. |
| 5,792,329 A | 8/1998 | Curé et al. |

OTHER PUBLICATIONS

Hsueh et al, J. Electrochem. Soc. 118(7), pp. 1128-1130, 1971.*
Patent Abstracts of Japan, vol. 1998, No. 09, Jul. 31, 1998 & JP 10 104196, Apr. 24, 1998.

* cited by examiner

SOLID ELECTROLYTE SENSOR FOR MONITORING THE CONCENTRATION OF AN ELEMENT IN A FLUID PARTICULARLY MOLTEN METAL

This application is the US national phase of international application PCT/GB02/01448 filed 25 Mar. 2002 which designated the U.S.

FIELD OF INVENTION

The present invention relates to an electrochemical sensor for determining the concentration of an element (eg. a Group 1A metal such as sodium or potassium) in a fluid, for example a molten metal. The molten metal may, for example, be aluminium or an aluminium alloy, but the invention is generally applicable to other metals and alloys, and to other fluids.

BACKGROUND OF INVENTION

The invention in a first aspect is, however, preferably concerned with the detection of sodium in molten aluminium or aluminium alloys, and although it will be appreciated that the invention is not limited thereto, for convenience it will be described with specific reference to these metals.

Sodium is often added to aluminium or aluminium alloys as a structural modifier in order to improve the physical properties of the metal. It is generally necessary to determine the concentration of the sodium in the metal melt so that the desired concentration may be arrived at.

Various designs of electrochemical sensor have been proposed in the past. For example, UK Patent No. 1470558 discloses an apparatus for detecting an element in a substance, in which a reference material is a solid electrolyte comprising a β-alumina compound of the element, or a solid compound of the element, such as a tungstate, molybdate or vanadate, separated from the substance by the β-alumina compound.

UK Patent No. 1602564 discloses a modification of the apparatus disclosed in the above mentioned patent, in which a β-alumina compound of the element to be detected is fused into the end of a tube of refractory material to provide a sealed tubular probe.

European Patent No. EP 0 679 252 B1 discloses a sensor for the measurement of trace elements in molten metals or alloys which has a solid electrolyte formed from zirconia toughened strontium β-alumina. The sensor may, for example, act as a sensor for sulphur, in which case it may incorporate a reference material comprising a mixture of molybdenum metal and molybdenum sulphide powders, which provides a fixed sulphur partial pressure against which the activity of the sulphur in the molten metal is measured.

SUMMARY OF INVENTION

It is an object of the present invention to provide a sensor which obviates or mitigates one or more disadvantages of the known sensors and which preferably offers one or more of the following specific advantages: durability, accuracy, repeatability and fast response time.

According to a first aspect, the present invention provides an electrochemical sensor for determining the concentration of a group IA metal in a fluid, comprising a substantially pure quantity of the group 1A metal contained in the sensor as a reference electrode, and a solid electrolyte providing at least part of the containment of the reference electrode, said sensor being capable of operating at temperatures in excess of 973K.

The use of pure sodium as a reference electrode has been proposed for low temperature applications, but it has not previously been considered technically feasible to devise a sensor for use at temperatures above 973K (Zhang et. al. Metallurgical and Materials Transactions, 27B, 795, 1996).

The sensors according to the various aspects of the invention operate as Nernstian potentiometric cells, in which the solid electrolyte separates the reference electrode, which has a known chemical activity of the element (e.g. sodium) being measured ($a_{El(Ref)}$), from the fluid (e.g. a molten metal or alloy) in which the sensor is immersed in use, which has an unknown chemical activity of the element being measured ($a_{El(Working)}$). The reversible electrical potential of such a cell is governed by the Nernst equation, which provides the theoretical relationship between the potential (E) and the relative activities of the reference and working electrodes, as follows:

$$E = (RT/zF) * \ln(a_{El(Ref)}/a_{El(Working)})$$

where:
E=the electrical potential (V)
R=the Molar Gas Constant (8.3144 Jmol$^{-1}$K$^{-1}$)
T=the absolute temperature (K)
z=the number of electrons transferred in the chemical system being measured
F=the Faraday Constant (96,485 Cmol$^{-1}$)
$a_{El(Ref)}$=the chemical activity of the reference electrode (the substantially pure element)
$a_{El(Working)}$=the chemical activity of the element in the working electrode (the fluid)

A plot of the electrical potential (the sensor voltage) versus the natural log of the ratio of the element activities of the reference and working electrodes would yield a straight line with a Nernst slope of (RT/zF). Since the electrical potential (the voltage) is measured by the sensor, and the temperature of the fluid in which the sensor is immersed (and hence the temperature of the sensor, including the solid electrolyte and reference electrode) may be measured, the only unknown is the chemical activity of the element in the fluid, and this may be calculated from the Nernst equation. The concentration of the element in the fluid may then be determined from the chemical activity of the element in the fluid.

For embodiments of the invention in which the sensor determines the sodium (or other group 1A metal) concentration in the fluid, z=1, the activity of a substantially pure sodium (or other group 1A) reference electrode=1, and the Nernst equation for the system is as follows:

$$E = (RT/F) * \ln(1/a_{Na(working)})$$

It was mentioned above that a preferred element to be detected by the sensor according to the first aspect of the invention is sodium. Consequently, the reference electrode preferably comprises substantially pure sodium.

It was also mentioned above that the fluid in which the sensor is immersed in order to determine the concentration of an element in the fluid, is preferably a molten metal (which term includes alloys). Particularly preferred molten metals include aluminium and aluminium alloys (eg. Al.Si alloys).

The reference electrode is contained in the sensor (as part of the sensor), and at least part of the containment of the reference electrode is provided by the solid electrolyte. The solid electrolyte preferably defines a containment wall forming at least a part of a housing, vessel or other container. The container formed (at least in part) from solid electrolyte may, for example, be generally tubular in shape, with a closed end, for example, the container may be generally cup-shaped. The solid electrolyte material generally does not fully enclose the space within the container, and the or each open portion of the container is preferably sealed by other means. Since the sensor is preferably used in molten metal, it will normally be required to withstand elevated temperatures, and therefore the solid electrolyte and any sealing means for sealing the container are preferably formed from refractory materials.

A preferred material for the solid electrolyte is an alumina-based material, and preferably a β-alumina material, such as a β"-alumina material. Advantageously, the β-alumina material may be toughened (eg. against thermal shock) by the incorporation of other elements, and zirconia toughened β"-alumina is especially preferred. The most preferred material for the solid electrolyte is zirconia toughened sodium β"-alumina.

As already mentioned, preferred materials for sealing one or more open portions of the solid electrolyte containment wall of the container comprise refractory materials. It is particularly preferred for the sealing material to comprise two or more oxides of the following elements: aluminium, calcium, magnesium, barium, boron and silicon.

A second aspect of the invention provides a process for the production of an electrochemical sensor for determining the concentration of an element (eg. a group 1A metal) in a fluid, comprising providing a sealed container, at least part of a containment wall of which comprises a solid electrolyte, and electrolytically introducing a substantially pure quantity of the element into the sealed container by passage of ions of the element through the solid electrolyte containment wall.

The electrolytic introduction of the element into the sealed container is preferably carried out by placing the container in a source of the element, in the case of a metal preferably a molten salt of the metal such as a nitrate, nitrite or hydroxide, or mixtures thereof, nitrite being preferred for safety reasons; a voltage is then applied across the solid electrolyte containment wall by means of a first electrical conductor which extends into the sealed container (the conductor is sealed into the container, for example by means of the refractory material referred to above) and which is in electrical contact with the internal surface of the solid electrolyte containment wall, and by means of another (second) electrical conductor which is immersed in the source of the element. This potential difference causes ions of the element to migrate through the solid electrolyte and into the sealed container. This is particularly useful where sodium is the element, for example, since it is a safe and effective way of introducing a precise quantity of sodium into the container (the first electrical conductor serving as a negative electrode). As an alternative, the first conductor need not extend into the container, but can be, for example, bonded or otherwise secured to that part of the container not constituted by the solid electrolyte.

In the case where the electrical conductor extends into the sealed container, it is preferably an elongate electrical conductor, and is preferably formed from one or more metals (which term includes alloys) such as platinum, niobium or nichrome. In order to enhance the electrical contact between the electrical conductor and the solid electrolyte containment wall inside the container (and hence to facilitate the electrolytic introduction of the group 1A metal into the container), some preferred embodiments of the invention include a conductive (electronic or ionic) substance located inside the container and in contact with the solid electrolyte and the elongate conductor. A preferred electrically conductive substance is carbon, especially carbon fibre, for example one or more carbon fibre discs. Other suitable conductive materials include silicon carbide, β-alumina powder, $TiO_2$ and graphite. Preferably, the atmosphere within the container is non-oxidising (especially when carbon is used) to prevent oxidation of the metal reference electrode material and carbon when present. As a result, the container contains little or no oxygen. For example, the container may contain a vacuum, but preferably it contains an inert (non-oxidising) gas, for example argon or nitrogen.

It will be understood that operation of the sensors of the present invention requires a counter electrode. The counter electrode functions as an electrical conductor when immersed in the fluid in order to enable the measurement of the electrical potential between the fluid and the reference electrode due to the difference in the chemical activities of the reference electrode and the metal being measured in the fluid. The counter electrode preferably is electrically insulated from the solid electrolyte to prevent short-circuiting (i.e. there is no direct electrical contact between the counter electrode and the solid electrolyte, the necessary electrical contact being via the fluid.

The counter electrode may form an integral part of the sensor. This arrangement enables the sensor to have a compact design, and is particularly useful, for example where the sensor is in the form of a probe to be dipped into the fluid. Preferably, the counter electrode is in the form of a ring or sheath surrounding part of the solid electrolyte container. The counter electrode may, for example, be bonded to the solid electrolyte by means of an electrically insulating adhesive, e.g. a ceramic cement. Alternatively, the counter electrode may be separated from the solid electrolyte by an electrically insulating (eg. ceramic) sleeve to which it is secured, the sleeve being secured to the solid electrolyte. Advantageously, the counter electrode may be formed, at least in part, from carbon (e.g. graphite).

In some preferred embodiments of the invention, the counter electrode may comprise an elongate housing for the solid electrolyte, with the solid electrolyte being located at a first end of the elongate housing, and the opposite end of the elongate housing arranged to be held outside the fluid (e.g. molten metal) while the first end is dipped into the fluid in order to determine the concentration of an element in the fluid. Alternatively, for example, the counter electrode (as well as the solid electrolyte) may be located only at the first end region of an elongate housing formed from one or more high temperature resistant materials, and the opposite end of the housing may be held outside the fluid. Suitable high temperature resistant materials include ceramic materials (e.g. ceramic fibres), silicon carbide and certain metals (e.g. steel encased within ceramic fibres or otherwise coated to prevent dissolution of the steel), since the housing needs only to be sufficiently temperature resistant to withstand the temperature of the fluid being tested (and, for example, a steel housing may generally be suitably temperature resistant where the fluid is aluminium or an aluminium alloy). A particularly preferred arrangement is one in which the solid electrolyte and the counter electrode are retained at a first end of an elongate metal (e.g. mild steel, nickel-plated to prevent oxidation) member (preferably a tube), and the elongate metal member is surrounded, along at least part of its length, by a ceramic sheath (preferably formed from ceramic fibres).

Where an elongate metal member is used, this may conveniently provide an electrical connection between the counter electrode and a voltmeter used to measure the electrical potential across the solid electrolyte. An elongate electrical conductor may extend through the elongate housing from the interior of the solid electrolyte to the voltmeter, for example.

It will be understood that in alternative arrangements, the counter electrode can be a separate component to the sensor itself, i.e. the counter electrode can be remote from the sensor, the two components being electrically connected in use. In some embodiments, particularly where the fluid is a molten metal, the counter electrode can be constituted by a conductive inner lining of the vessel in which the fluid is contained.

A third aspect of the invention provides a durable electrochemical sensor for determining the concentration of an element in a fluid, comprising a sealed container containing a quantity of the element or compound of the element as a reference electrode, at least part of a containment wall of the container being formed from a solid electrolyte, and an elongate electrical conductor which comprises a first portion formed from a first electrically conductive material and a second portion formed from a second, different, electrically conductive material, wherein the first portion is in electrical contact with the reference electrode and extends from the reference electrode to within a seal of the container, and the second portion extends from within the seal to the outside of the container, the first and second portions being in electrical contact with each other.

The third aspect of the invention has the advantage that the first electrically conductive material of the elongate conductor may be a material which is capable of withstanding contact with the material of the reference electrode, whereas the second material of the elongate conductor may be a material which is inert in air. For example, where the reference electrode comprises sodium under a non-oxidising atmosphere, the first electrically conductive material may be niobium or a niobium alloy, since niobium is resistant to sodium, whereas the second material may for example be a metal which is inert in air, such as platinum or a platinum alloy (e.g. platinum/rhodium). Niobium is oxidised in air, hence it would be unsuitable for use outside the container, and platinum is attacked by sodium, hence it would be less suitable in terms of durability for use inside the container.

The seal of the solid electrolyte container is preferably a refractory material, more preferably a calcium aluminate-based material.

The sensors according to the first or third aspects of the invention may be used, for example, in a process of adding an element (for example sodium) to a fluid (for example a molten metal, especially aluminium or an aluminium alloy), in order to determine when the required amount of the element has been added to the fluid.

A fourth aspect of the invention consequently comprises a process for the controlled addition of a predetermined amount of an element to a molten metal, comprising the steps of:—

(i) adding a quantity of the element corresponding to the predetermined amount to the molten metal, (ii) monitoring the actual quantity of the element achieved in the molten metal using a sensor in accordance with the present invention, (iii) adding further quantities of the element until the level measured in step (ii) corresponds to the predetermined amount.

It will be understood that the level of element (eg. sodium) achieved in the molten metal (eg. aluminium) is likely to decrease over a period of time and be less than the quantity initially added because of losses by, for example, evaporation. For example, in a casting operation, the level of sodium at the time of casting will be less than in the ladle. The sensors of the present invention have a fast response time and allow the real-time monitoring of the quantity of the element being detected. Thus, the output from the sensor can be used as feedback to allow the amount of the element added to the molten metal to be continuously varied so as to maintain the level in the molten metal at the predetermined value.

A fifth aspect of the invention comprises an apparatus for adding an element to a fluid, the apparatus including a sensor according to the first or third aspects of the invention.

BRIEF DESCRIPTION OF ACCOMPANYING DRAWINGS

Figure 2:
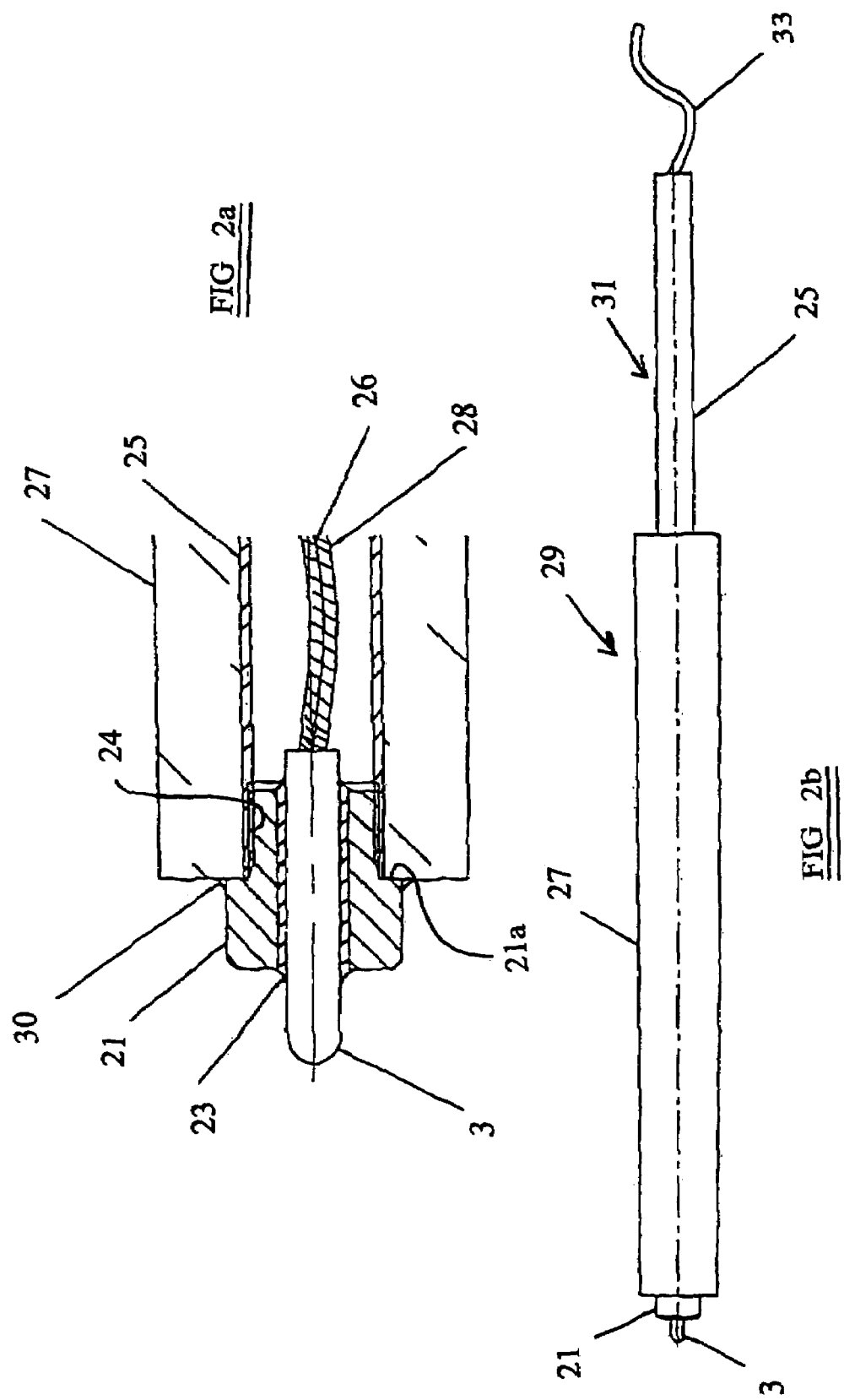
Figure 3:
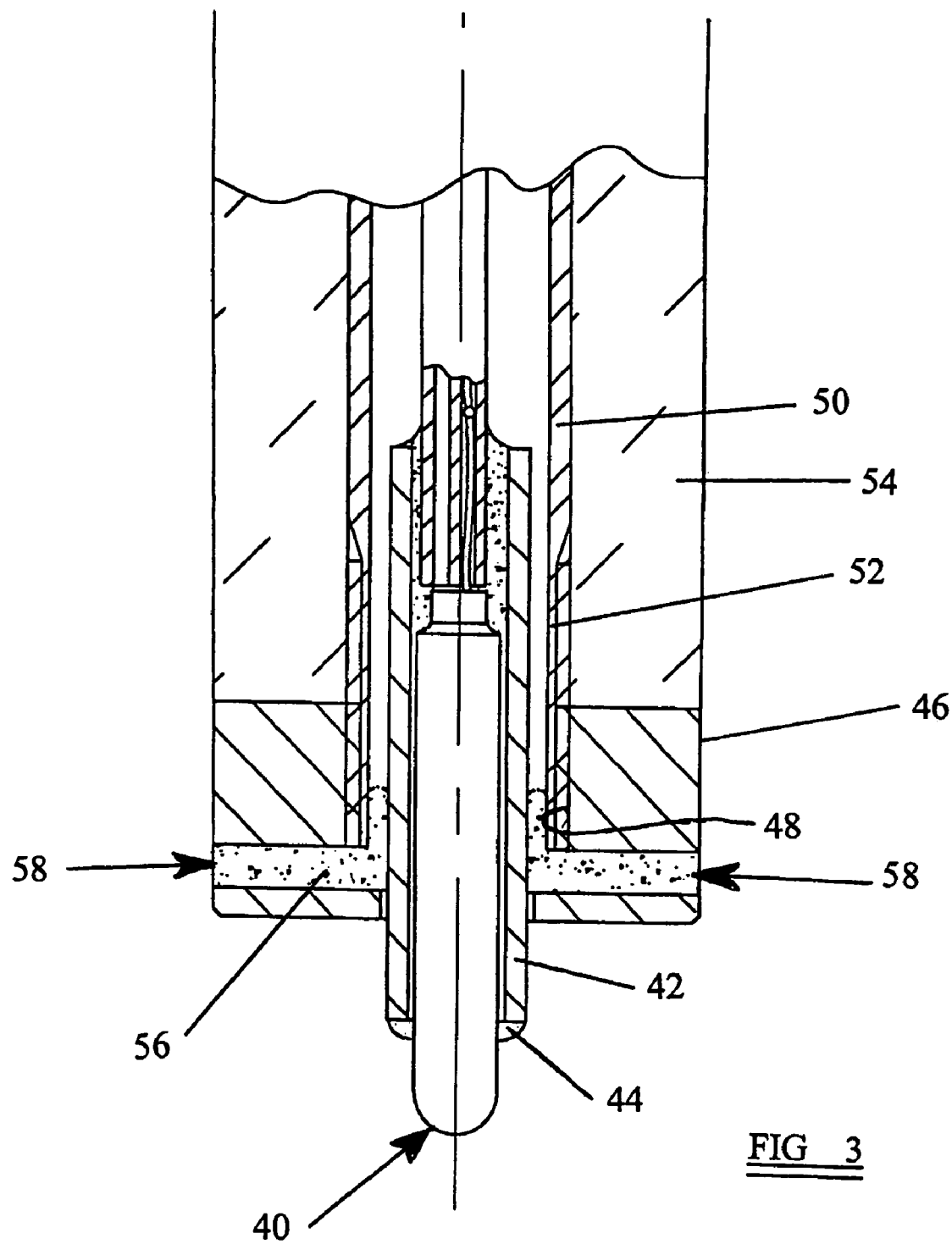
Figure 4:
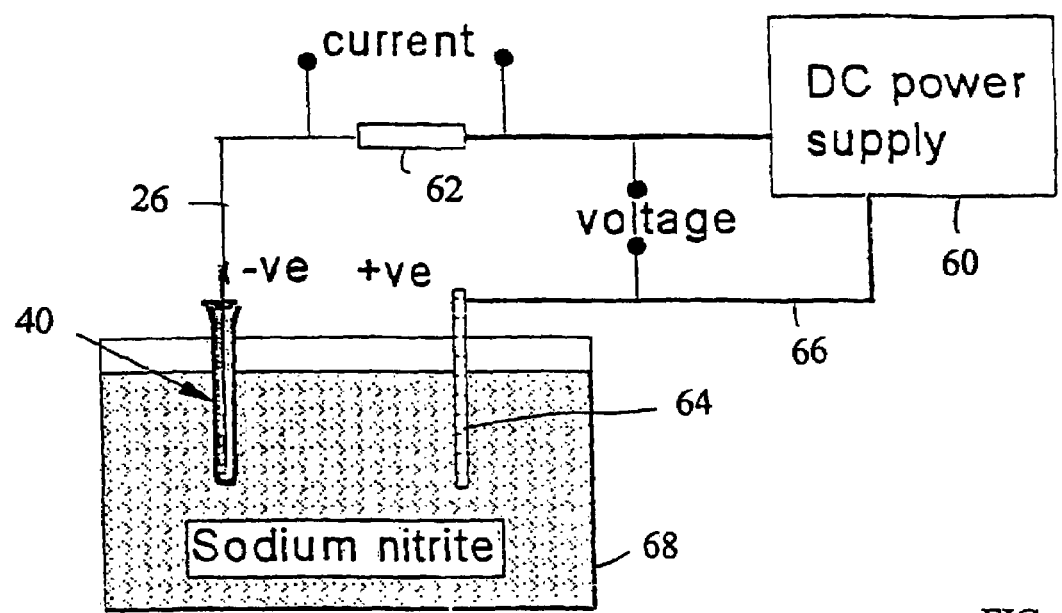
Figure 5:
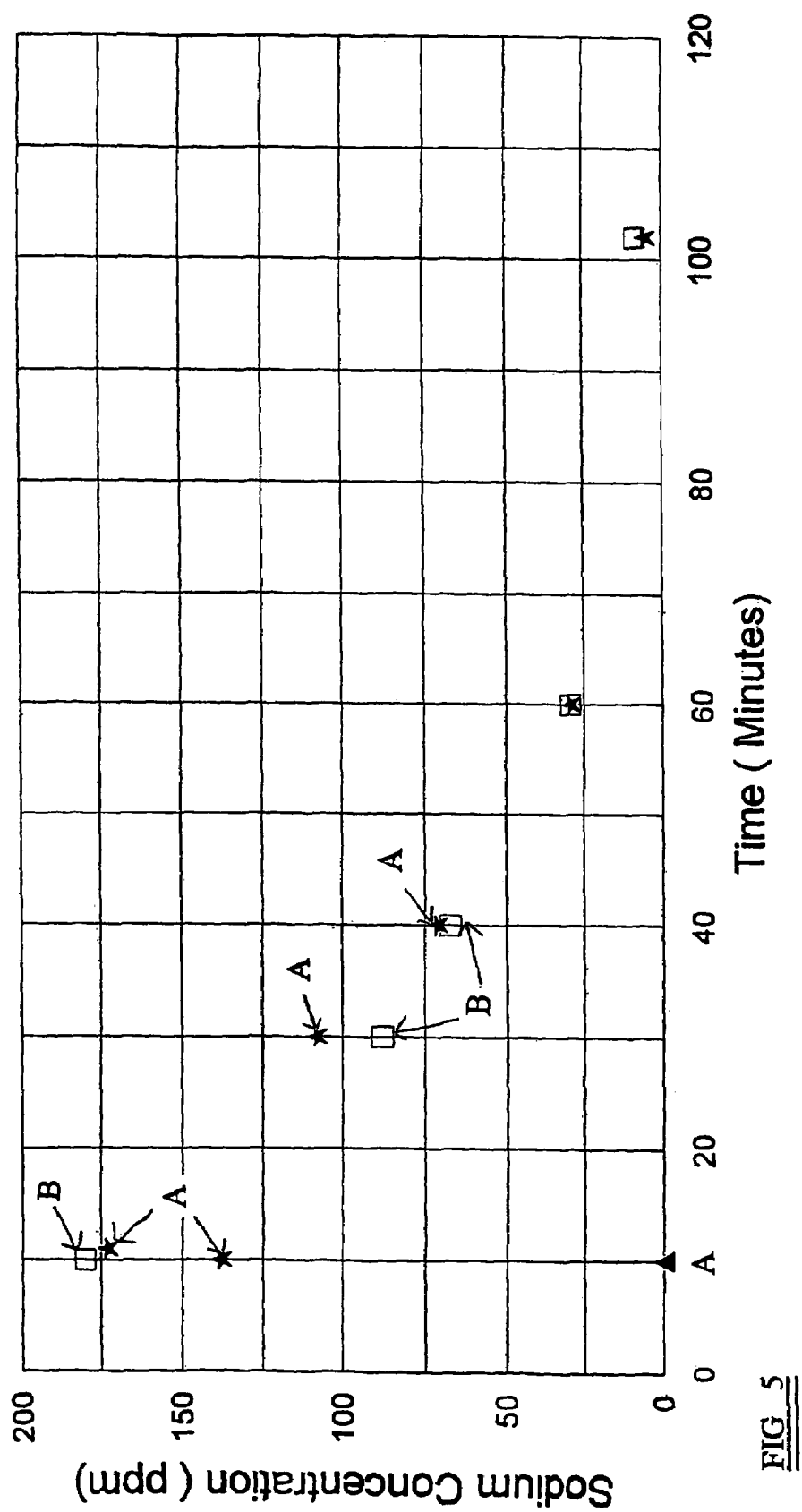
Figure 6:
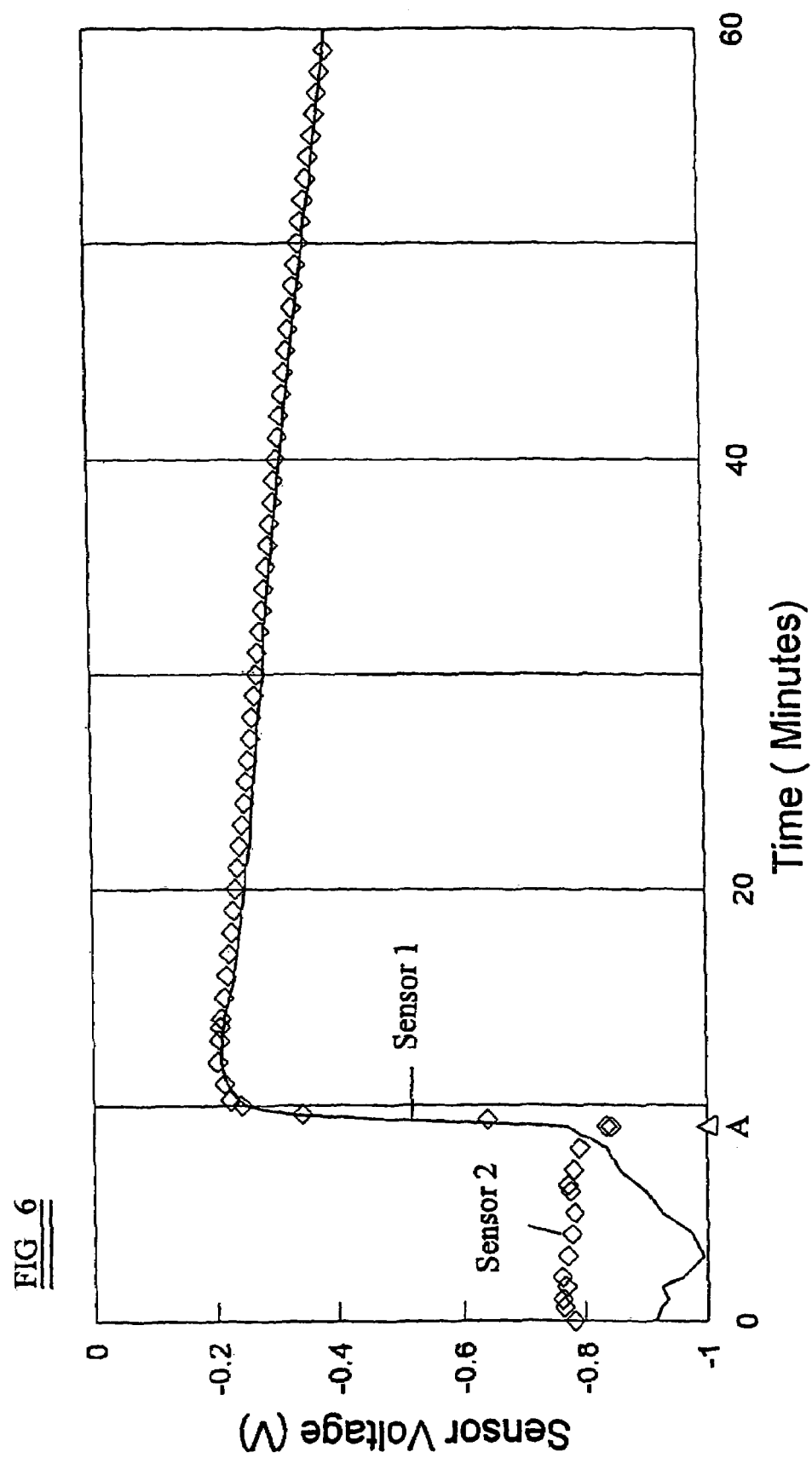
Figure 7:
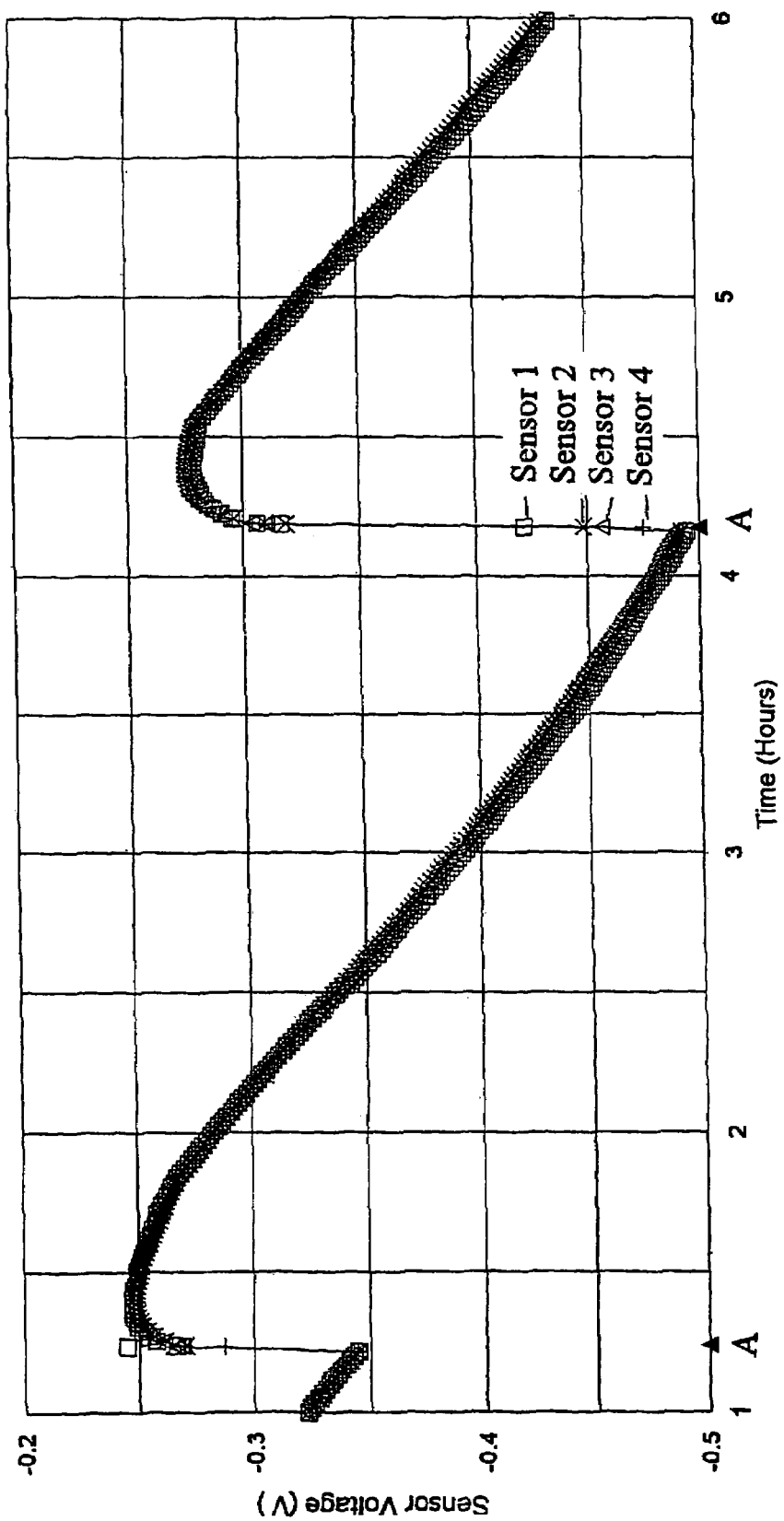
Figure 8:
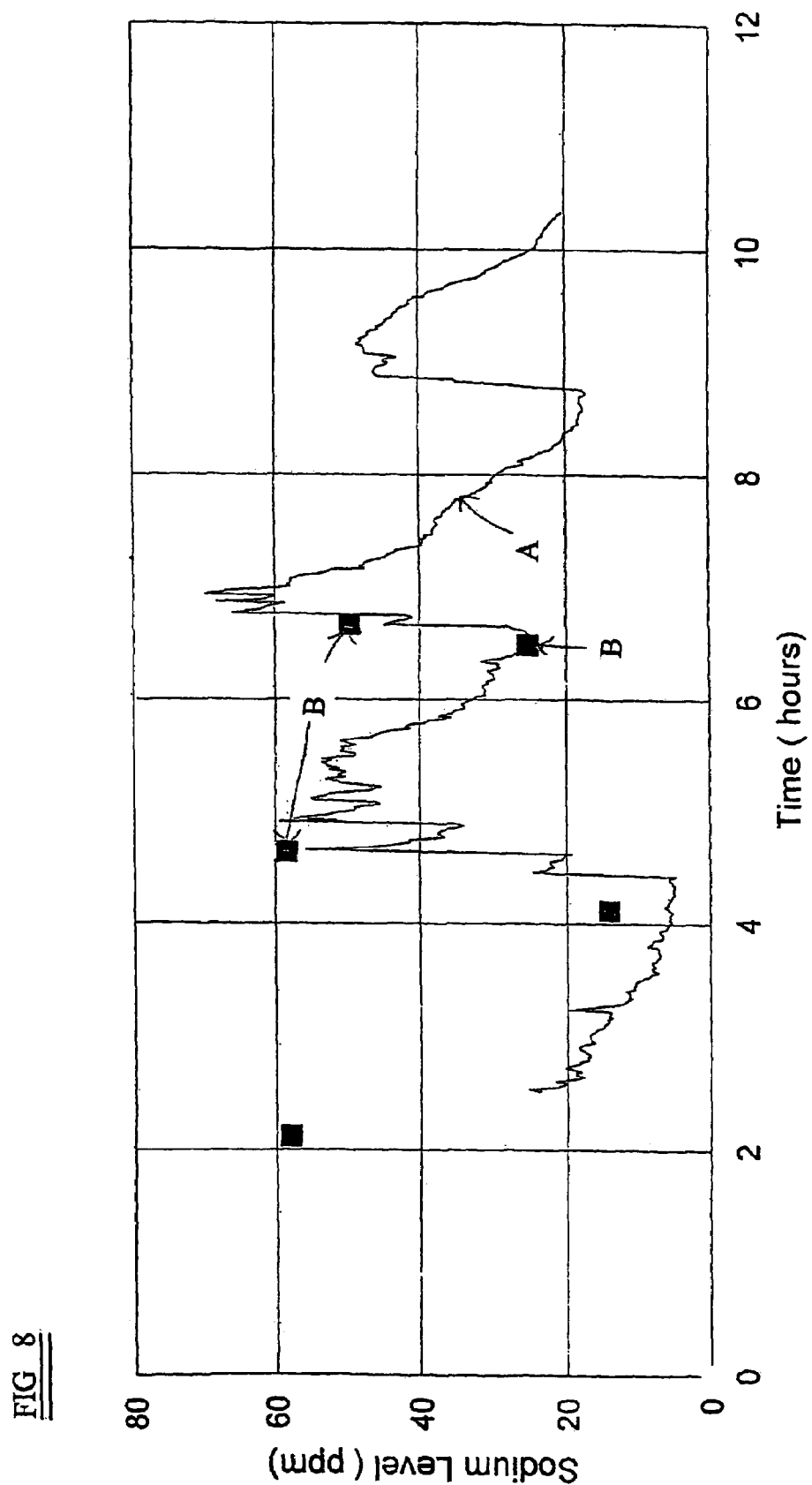
Figure 9:
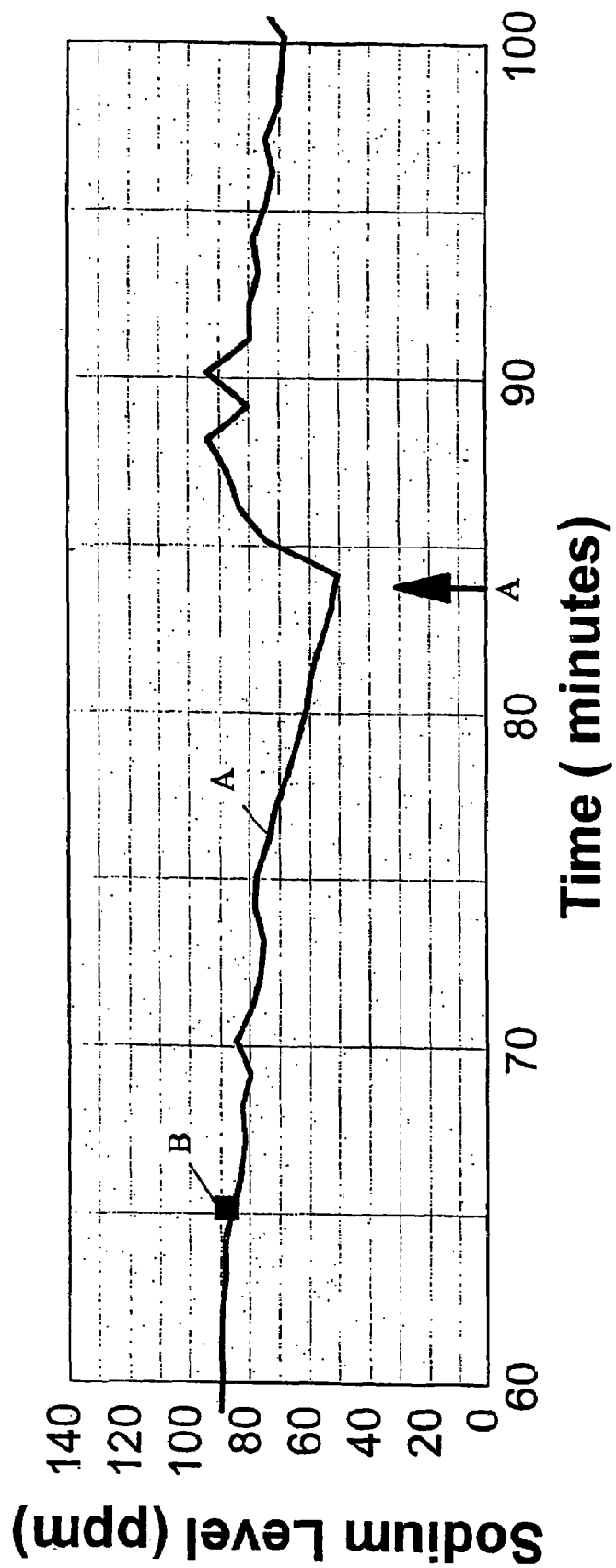

Embodiments of the present invention will now be described, by way of example only, with reference to the accompanying drawings in which:

FIG. 1 is a cross-sectional illustration of a detail of a sensor according to the invention, FIG. 2a shows a view of a sensor according to the present invention, FIG. 2b is a detail view of part of the sensor shown in FIG. 2a, FIG. 3 is a cross-sectional view of part of another sensor in accordance with the present invention, FIG. 4 is a schematic representing the electrolytic filling of a sensor in accordance with the present invention, FIG. 5 is a comparative plot of sodium concentration against time as determined by a sensor in accordance with the present invention and as determined by spectrometric analysis for a sodium containing Al.Si melt, FIG. 6 is a plot of sensor voltage against time for two similar sensors in molten Al.Si alloy containing sodium, FIG. 7 is a plot of sensor voltage against time for four similar sensors in molten Al.Si alloy, FIG. 8 is a plot of sodium concentration against time as measured by a sensor in accordance with the present invention with variable sodium additions to an Al.Si melt, and FIG. 9 is a plot of sodium concentration against time as determined by a sensor in accordance with the present invention for a sodium containing Al.Si melt.

DETAILED DESCRIPTION OF PREFERRED EMBODIMENTS

FIG. 1 shows a detail of a sensor 1 according to the invention, for determining the concentration of sodium in molten aluminium. The sensor 1 comprises a container 3 formed from zirconia toughened sodium β"-alumina solid electrolyte. The container 3 is in the form of a generally cup-shaped vessel, i.e. it comprises a tube have a closed end 5 and an open end 7 which is sealed by means of a refractory tube 9 formed from α-alumina and an inner seal 11a formed from calcium aluminate refractory material. Sealing is effected between the outer circumference of the refractory tube 9 and container 3 by an outer (annular) seal 11b also formed from calcium aluminate refractory material. The container 3 consequently is hermetically sealed and contains argon gas (rather than air) above the sodium (as indicated by reference numeral 12). The sealed container contains a substantially pure quantity of sodium 13 which acts as a reference electrode; the sodium has been introduced into the container 3 electrolytically, as described below. The container also contains a plurality of carbon fibre discs (not shown) which facilitate the electrolytic introduction of the sodium. Extending into the sealed container 3 from its exterior is an elongate electrical conductor 15 for providing an electrical connection between the sodium reference electrode and a voltmeter (not shown). The electrical conductor 15 comprises a first portion 17 formed from niobium, this first portion extending from the sodium reference electrode 13 to within the refractory seal 11a, and a second portion 19 formed from platinum, the second portion 19 extending from within the refractory seal 11a to the exterior of the container 3. The first and second portions 17,19 of the electrical conductor 15 are joined together (by welding) within the refractory seal 11a. As described earlier, the niobium is resistant to chemical attack from the sodium (but would be oxidised in air) and the platinum is inert in air but would be attacked by the sodium. In addition, the niobium has a comparable thermal expansion coefficient to the calcium aluminate seal 11a, producing a thermally cycleable hermetic seal, and thus reducing the possibility of sodium ingress into the seal 11a. It should be noted that an oxide interface exists between the niobium and the seal 11a, and this is also chemically resistant to sodium. The sealed container 3 and electrical conductor 15 will hereinafter be referred to as the "sensor head".

FIG. 2b shows a sensor assembly according to the invention (no voltmeter or other ancillary electrical equipment, such as a computer, are shown). FIG. 2a shows an enlarged detail of the sensor shown in FIG. 2b, in which the electrolytic container 3 of the sensor head shown in FIG. 1 is surrounded by a counter electrode 21. The counter electrode 21 is formed from graphite and is in the form of a sheath surrounding part of the sensor head while leaving an end region of the sensor head exposed so that it may come into contact with the molten aluminium in use. The graphite sheath is bonded to the exterior of the container 3 by electrically insulating ceramic cement 23 and is stepped to form a region having a relatively large outer diameter and a region having a relatively narrow outer diameter, an annular abutment surface 21a being defined therebetween. The region of relatively narrower diameter is provided with an external screw thread 24. The screw-threaded counter electrode 21 is threadably attached to a first end of a correspondingly threaded steel tube 25 such that the steel tube 25 abuts the annular abutment surface 21a of the counter electrode 21 and an electrical lead wire 26 made of nickel (which is enclosed in insulation 28) which is welded at a free end to the platinum portion 19 of the conductor 15 extends through the interior of the steel tube 25. It will be understood that the conductor 15 could be made sufficiently long to extend through the steel tube 25, but nickel is less expensive than platinum. The insulation 28 protects the wire 26 from heat and possible oxidation at elevated temperature. It will be understood therefore that the steel tube 25 is in good electrical contact with the counter electrode 21. The steel tube 25 is itself surrounded by an outer ceramic fibre sheath 27, and the steel tube 25 and ceramic fibre sheath 27 together constitute an elongate refractory housing 29. The ceramic fibre sheath 27 rests on the annular abutment surface 21a of the counter electrode 21, and a seal is formed therebetween by a bead of ceramic insulating cement 30. The sheath 27 is a push fit over the metal tube 25 and is held in place by means of the ceramic cement bead 30. The entire housing 29 is shown in FIG. 2b, from which it can be seen that the ceramic fibre sheath. 27 surrounds the steel tube 25 for only part of its length, a region 31 of the steel tube 25 remote from the sensor head being exposed because the ceramic fibre sheath 27 is not required in this region 31 since this region 31 will not be immersed in the molten aluminium. An electrical contact wire connected to the steel tube 25 (and therefore the graphite counter electrode) and the lead wire 26 are indicated by reference numeral 33. These wires are connected to a voltmeter (not shown) and it will be understood that when immersed in molten aluminium, an electrical circuit is completed.

Referring to FIG. 3, a modified sensor assembly is shown. The sensor head 40 is as described with reference to FIG. 1. The sensor head 40 is a close sliding fit within an alumina insulating ceramic sleeve 42, an end of the sensor head being exposed. The sleeve 42 is secured to the sensor head 40 by means of an annular bead 44 of insulating ceramic cement which also serves to prevent ingress of molten aluminium in use.

An annular carbon counter electrode 46 having an internal screw thread 48 is threadingly engaged onto an end of a thin walled nickel-plated mild steel tube 50 having a corresponding external screw thread 52. A ceramic fibre sheath 54 is a push fit over the metal tube 50, the sheath 54 and carbon electrode 46 being of substantially the same diameter. A thin layer of ceramic cement (not shown) is provided between the carbon electrode 54 and the ceramic fibre sheath 54 to prevent ingress of molten alumnium. The sensor head 40 and insulating ceramic sleeve 42 assembly is located within the steel tube 50 such that the cemented end of the sleeve 42 (and the exposed end of the sensor head 40) projects beyond the carbon electrode 46. The sensor head/insulating sleeve assembly is held in place by insulating cement 56 applied through a pair of drillings 58 provided on a diameter through the carbon electrode 46.

The embodiment described with reference to FIG. 3 has two important advantages over that described in relation to FIG. 2a:—
1. The sensor head 40 and counter electrode 46 are separated by an insulating sleeve 42 which is more effective in insulating electrical contact between the sensor head 40 and the counter electrode 46. Unlike cement, the sleeve 42 is not prone to being worn or washed away.
2. A relatively large diameter carbon electrode 46 is employed. In use, under the stringent operating conditions, the carbon electrode 46 tends to crumble. The provision of a large electrode significantly extends the sensor life.

The filling of the sensor with sodium is effected on the sensor head 40 prior to assembly with the various holder arrangements. Referring to FIG. 4, the sensor head 40 is first weighed and the lead 26 in electrical contact with the solid electrolyte is connected to the negative terminal of a DC power supply 60. An accurate shunt resistor 62 is connected in series between the DC power supply and the sensor head 40 so that the charge current can be accurately measured during the filling process. A steel wire electrode 64 is connected to the positive terminal of the DC power supply by a second lead 66. The sensor head 40 and steel electrode 64 are immersed in a heated bath 68 of molten sodium nitrite (mp 271° C.) which is equipped with a thermocouple (not shown) to accurately monitor the bath temperature. A eutectic mixture of sodium nitrate and sodium nitrite (32:68 mol %) can also be used, allowing filling to take place at a lower temperature (226° C.) and a voltage and current are applied across the sensor head 40 and the steel electrode 64 until the charging current reaches a desired level. The sensor is conveniently filled in a constant current mode at a current of between 50 and 100 mA. Typically about 0.1 to 0.2 g of sodium is filled.

During filling, the current, voltage and temperature are logged and the quantity of sodium added is calculated from the integrated charge current. After residual salt has been removed from the external surfaces of the sensor head 40, the sensor head 40 is reweighed as confirmation of the calculated amount of sodium added.

The accuracy, response time and reproducibility of the sensor heads filled according to the above method were then assessed. In all tests the sensor head was preheated prior to immersion in the melt to avoid thermal shock and the possibility of fracture. It is known that subcritical damage can occur with β-alumina ceramics if they are exposed to thermal shocks of greater than 200° C. Although auxiliary pre-heating (eg. using a gas flame) can be adopted, it was found to be more convenient to use the radiant heat from the melt itself. Thus, the sensor head was held approximately 10 mm above the melt for about two minutes, approximately 3 to 5 mm above the melt for a further minute and then immersed slowly into the melt.

Test 1

Referring to FIG. 5 a quantity of sodium was added (point A) to a stirred Al.Si7% alloy melt at 735° C. The concentration of sodium in the melt was measured at intervals using a spark emission spectrometer and a sensor head as described with reference to FIG. 1 (the sensor head was cemented to an α-alumina holder and an α-alumina protection tube was provided around the lead wires from the sensor head). As can be seen from FIG. 5 the concentration of sodium within the melt diminished over time and the values derived from the sensor (arrows A) were in good agreement with those measured by the spectrometer (arrows B).

Test 2

Referring to FIG. 6, two sensors of the same design as that used in test 1 were immersed in an alloy of the same composition and at the same temperature as described for test 1. Sodium was added to the melt (point A) and the sensor voltages measured for one hour. As can be seen from FIG. 6, both sensors responded very quickly to the increase in sodium concentration (<1 min) and the two sensors were in good agreement as the concentration of sodium gradually decreased due to evaporation losses.

Test 3

Referring to FIG. 7, an Al.Si7% melt was stirred at 700° C. and two batches of sodium were added (points A) with a four hour interval therebetween. Four sensor heads were immersed in the melt (heads mounted on 60% α-alumina tubes) and the sensor voltages measured. As can be seen from FIG. 7, all four sensors were in close agreement and all four sensors responded rapidly to each of the sodium additions.

Test 4

The sensors of the present invention are useful at even higher temperatures than described above. Referring to FIG. 8, sodium additions (variable) were made to an Al.Si10% alloy at 800° C. The sensor determination of sodium level (arrow A) was plotted against the sodium level as determined by spectrometer (arrow B) in FIG. 8 with good agreement being found.

In each of tests 1 to 4, the counter electrode was a remote carbon electrode.

Test 5

Referring to FIG. 9, a sensor as described with reference to FIG. 3 was used to measure the sodium concentration of an AlSi10% alloy at 775° C. As with the previous tests, the sensor (plot A) was in good agreement with chemical (spectrometer) analysis (plot B) and a rapid response was observed on addition of sodium (arrow A).

The invention claimed is:

1. A durable electrochemical sensor for determining the concentration of an element in a fluid, comprising a sealed housing containing a quantity of the element or a compound of the element as a reference electrode, at least part of the housing being formed from a solid electrolyte, and an elongate electrical conductor which comprises a first portion formed from a first electrically conductive material and a second portion formed from a second, different, electrically conductive material, wherein the first portion is in electrical contact with the reference electrode and is chemically compatible therewith and extends to within a seal of the housing, and the second portion extends from within the seal to the outside of the housing, the first and second portions being in electrical contact with each other, wherein the reference electrode is a substantially pure group 1A metal and the first electrically conductive material is niobium or a niobium alloy.

2. A durable electrochemical sensor as claimed in claim 1, wherein the second material of the elongate conductor is a material which is inert in air.

3. A durable electrochemical sensor as claimed in claim 2, wherein the second material is platinum or a platinum alloy.

4. A sensor as claimed in claim 1, wherein the sensor is mounted within an insulating housing, such that at least a part of said solid electrolyte is exposed.

5. A sensor as claimed in claim 1 additionally comprising a counter electrode.

6. A sensor as claimed in claim 5, wherein the counter electrode is secured to the sensor housing and electrically insulated from the solid electrolyte.

7. A sensor as claimed in claim 6, wherein an insulating sleeve is mounted between the counter electrode and the solid electrolyte.

8. A sensor as claimed in claim 5, wherein the counter electrode is graphite or silicon carbide.

\* \* \* \* \*